(12) United States Patent
Iannotti et al.

(10) Patent No.: US 10,918,442 B2
(45) Date of Patent: Feb. 16, 2021

(54) GLENOID COMPONENT FOR SHOULDER ARTHROPLASTY

(71) Applicant: DePuy Synthes Products, Inc., Raynham, MA (US)

(72) Inventors: Joseph P. Iannotti, Strongsville, OH (US); Kimerly A. Powell, Powell, OH (US); Gerald R. Williams, Villanova, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 124 days.

(21) Appl. No.: 16/240,177

(22) Filed: Jan. 4, 2019

(65) Prior Publication Data

US 2019/0133691 A1    May 9, 2019

Related U.S. Application Data

(60) Division of application No. 14/726,717, filed on Jun. 1, 2015, now Pat. No. 10,182,867, which is a
(Continued)

(51) Int. Cl.
*A61B 34/10* (2016.01)
*A61F 2/40* (2006.01)
*G06T 17/00* (2006.01)
*B33Y 80/00* (2015.01)
*A61F 2/30* (2006.01)

(52) U.S. Cl.
CPC ............ *A61B 34/10* (2016.02); *A61F 2/4081* (2013.01); *G06T 17/00* (2013.01); *A61F 2/3094* (2013.01); *A61F 2002/30156* (2013.01); *A61F 2002/30604* (2013.01); *A61F 2002/30948* (2013.01); *A61F 2002/30952* (2013.01); *A61F 2002/30957* (2013.01); *A61F 2002/30962* (2013.01); *A61F 2230/0023* (2013.01); *A61F 2240/002* (2013.01); *B33Y 80/00* (2014.12); *Y10T 29/49* (2015.01)

(58) Field of Classification Search
CPC .. A61F 2/30; A61B 5/05; A61B 19/00; G06T 17/00
USPC .......................................... 623/19.11–19.14
See application file for complete search history.

(56) References Cited

U.S. PATENT DOCUMENTS 3,061,977 A    11/1962    Schmidt
5,150,304 A     9/1992    Berchem et al.
(Continued)

FOREIGN PATENT DOCUMENTS

EP    1402853 A2    3/2004
EP    1639967 A1    3/2006
(Continued)

*Primary Examiner* — Yashita Sharma
(74) *Attorney, Agent, or Firm* — Maginot, Moore & Beck, LLP

(57) ABSTRACT

A glenoid component includes a laterally facing bearing surface configured to engage a bearing surface of an element associated with a humerus, and a stem portion extending medially away from the bearing surface. The stem portion is configured such that when implanted in a scapula the stem portion includes three cross-sections parallel to a medial lateral plane. The middle cross-section has a length in the medial-lateral direction which is shorter than the lengths of the other two cross-sections in the medial lateral direction.

12 Claims, 14 Drawing Sheets

Related U.S. Application Data continuation of application No. 12/565,039, filed on Sep. 23, 2009, now abandoned, which is a continuation of application No. 11/524,335, filed on Sep. 20, 2006, now Pat. No. 7,604,665.

(56) References Cited

U.S. PATENT DOCUMENTS

| | | |
|---|---|---|
| 6,488,715 B1 | 12/2002 | Pope et al. |
| 2002/0004685 A1 | 1/2002 | White |
| 2003/0055507 A1* | 3/2003 | McDevitt .............. A61F 2/4081 623/19.11 |
| 2004/0064189 A1 | 4/2004 | Maroney et al. |
| 2004/0220674 A1 | 11/2004 | Pria |
| 2004/0236424 A1 | 11/2004 | Berez et al. |
| 2006/0100498 A1 | 5/2006 | Boyce et al. |

FOREIGN PATENT DOCUMENTS

| | | |
|---|---|---|
| FR | 2825263 | 12/2002 |
| GB | 2297257 | 7/1996 |

\* cited by examiner

|  | NUMBER OF VAULTS | SUPERIOR-INFERIOR DIMENSION | | |
|---|---|---|---|---|
|  |  | MINIMUM (mm) | MAXIMUM (mm) | AVERAGE (mm) |
| GROUP 1 | 5 | 24.85 | 27.05 | 26.13 |
| GROUP 2 | 14 | 27.81 | 30.36 | 29.36 |
| GROUP 3 | 13 | 31.27 | 32.66 | 31.90 |
| GROUP 4 | 14 | 33.08 | 35.93 | 34.42 |
| GROUP 5 | 10 | 35.98 | 38.88 | 37.27 |
| GROUP 6 | 5 | 39.24 | 40.17 | 39.63 |

SUPERIOR

3D VIEW

LATERAL

ANTERIOR

| CROSS SECTION REFERENCE NO. | WIDTH, "w" (mm) | DEPTH, "d" (mm) | AREA (mm$^2$) |
|---|---|---|---|
| 1840 | 10.01 | 28.50 | 140.81 |
| 1860 | 22.27 | 19.75 | 221.69 |
| 1880 | 22.26 | 18.00 | 201.97 |
| 1900 | 17.51 | 20.75 | 206.32 |
| 1920 | 10.51 | 22.50 | 121.63 |

FIG. 12

| CROSS SECTION REFERENCE NO. | VERTEX REFERENCE NO. | X COORDINATE (mm) | Y (mm) | Z (mm) |
|---|---|---|---|---|
| 1840 | 2020 | 28.50 | 8.25 | 0.000 |
| | 2000 | 0.00 | 15.00 | 0.000 |
| | 2040 | 28.00 | 18.25 | 0.000 |
| 1860 | 2080 | 29.25 | 1.00 | 8.125 |
| | 2060 | 8.75 | 13.75 | 8.125 |
| | 2100 | 28.25 | 23.25 | 8.125 |
| 1880 | 2140 | 29.00 | 0.50 | 16.250 |
| | 2120 | 10.50 | 10.75 | 16.250 |
| | 2160 | 28.25 | 22.75 | 16.250 |
| 1900 | 2200 | 28.75 | 2.50 | 24.375 |
| | 2180 | 7.75 | 6.75 | 24.375 |
| | 2220 | 28.25 | 20.00 | 24.375 |
| 1920 | 2240 | 29.00 | 3.50 | 32.500 |
| | 2260 | 6.00 | 0.00 | 32.500 |
| | 2280 | 28.50 | 14.00 | 32.500 |

FIG. 13

GLENOID COMPONENT FOR SHOULDER ARTHROPLASTY

CROSS-REFERENCE TO RELATED APPLICATIONS

This application is a divisional application of U.S. application Ser. No. 14/726,717, entitled "Glenoid Component For Shoulder Arthroplasty" by Iannotti et al., filed Jun. 1, 2015, which issued as U.S. Pat. No. 10,182,867 on Jan. 22, 2019, and which is a continuation application of U.S. application Ser. No. 12/565,039 entitled "Glenoid Component For Shoulder Arthroplasty" by Iannotti et al., filed Sep. 23, 2009 now abandoned, which is in turn a continuation application of U.S. application Ser. No. 11/524,335 entitled "Glenoid Component For Shoulder Arthroplasty" by Iannotti et al., filed Sep. 20, 2006 which issued as U.S. Pat. No. 7,604,665 on Oct. 20, 2009, the disclosures of which are hereby incorporated herein by reference in their entireties.

TECHNICAL FIELD

The present invention relates generally to the field of orthopedics, and, more particularly, to glenoid component apparatuses for shoulder arthroplasty and methods for making them.

BACKGROUND

Arthroplasty is the surgical replacement of one or more bone structures of a joint with one or more prostheses. Shoulder arthroplasty often involves replacement of the glenoid fossa of the scapula with a prosthetic glenoid component. The conventional glenoid component typically provides a generally laterally or outwardly facing generally concave bearing surface against which a prosthetic humeral head (or, alternatively, the spared natural humeral head in the case of a glenoid hemi-arthroplasty) may bear during operation of the joint. The conventional glenoid component typically also includes a generally medially or inwardly projecting stem for fixing the glenoid component in a cavity constructed by suitably resecting the glenoid fossa and suitably resecting cancellous bone from the glenoid vault.

Various stem designs have been proposed for ensuring proper alignment and secure and lasting fixation of the glenoid component within the glenoid vault. However, the glenoid vault has a complex morphology. While three-dimensionally shaping a stem for compatibility with the endosteal walls of the glenoid vault can potentially significantly enhance fixation of the glenoid component, historical designs have not taken full advantage of this opportunity.

One advantageous approach is described in co-pending application Ser. No. 10/259,045, published on Apr. 1, 2004 as US2004/0064189 A1 and entitled "Concave Resurfacing Prosthesis", the disclosure of which is incorporated herein by reference. In this approach, a glenoid component is fitted to at least partially fill a cavity formed in the glenoid vault. The component has a generally oval inverted dome shape to generally conform to the shape of the vault. However, it is recognized in the '045 application that exact sizing of the glenoid component to the vault cavity is made difficult by the unique anatomy of each patient. To address this difficulty, the '045 application discloses providing a series of differently sized glenoid components.

There remains a need for a glenoid component that is more nearly sized and shaped in three-dimensions to fill the cavity in the glenoid vault. There is a further need for a technique that facilitates preparation of such a component, and especially a component that has more universal applicability to the anatomy of most patients.

SUMMARY OF THE INVENTION

The present invention provides a glenoid component apparatus for shoulder arthroplasty. The apparatus includes a bearing portion and further includes a stem portion extending from the bearing portion. The stem portion models a normalized or pathologic glenoid vault morphology.

In an alternative embodiment, the present invention provides a method for making a glenoid component for shoulder arthroplasty. The method includes obtaining a model of a normal or pathologic glenoid vault morphology and further includes producing a portion of the glenoid component based on the model.

In another alternative embodiment, the present invention provides a glenoid component apparatus for a shoulder joint including at least one of a natural humeral component and a prosthetic humeral component. The apparatus includes a means for bearing against at least one of the natural humeral component and the prosthetic humeral component. The apparatus further includes a means, extending from the bearing means, for modeling a normal glenoid vault morphology.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

BRIEF DESCRIPTION OF THE DRAWINGS

FIG. 5 shows a table listing exemplary range and exemplary average SI dimension for six exemplary sub-groups of scapulae from a scapulae sample based on their SI dimensions;

FIG. 12 shows a table listing the respective width dimension, depth dimension, and resulting area of the triangular cross sections of the simplified 3-D model of FIG. 10; and FIG. 13 shows a table listing the coordinates for the respective vertexes of the triangular cross sections of the simplified 3-D model of FIG. 10 relative to the rectangular ("Cartesian") coordinates reference system of FIG. 3.

DETAILED DESCRIPTION

Figure 1:
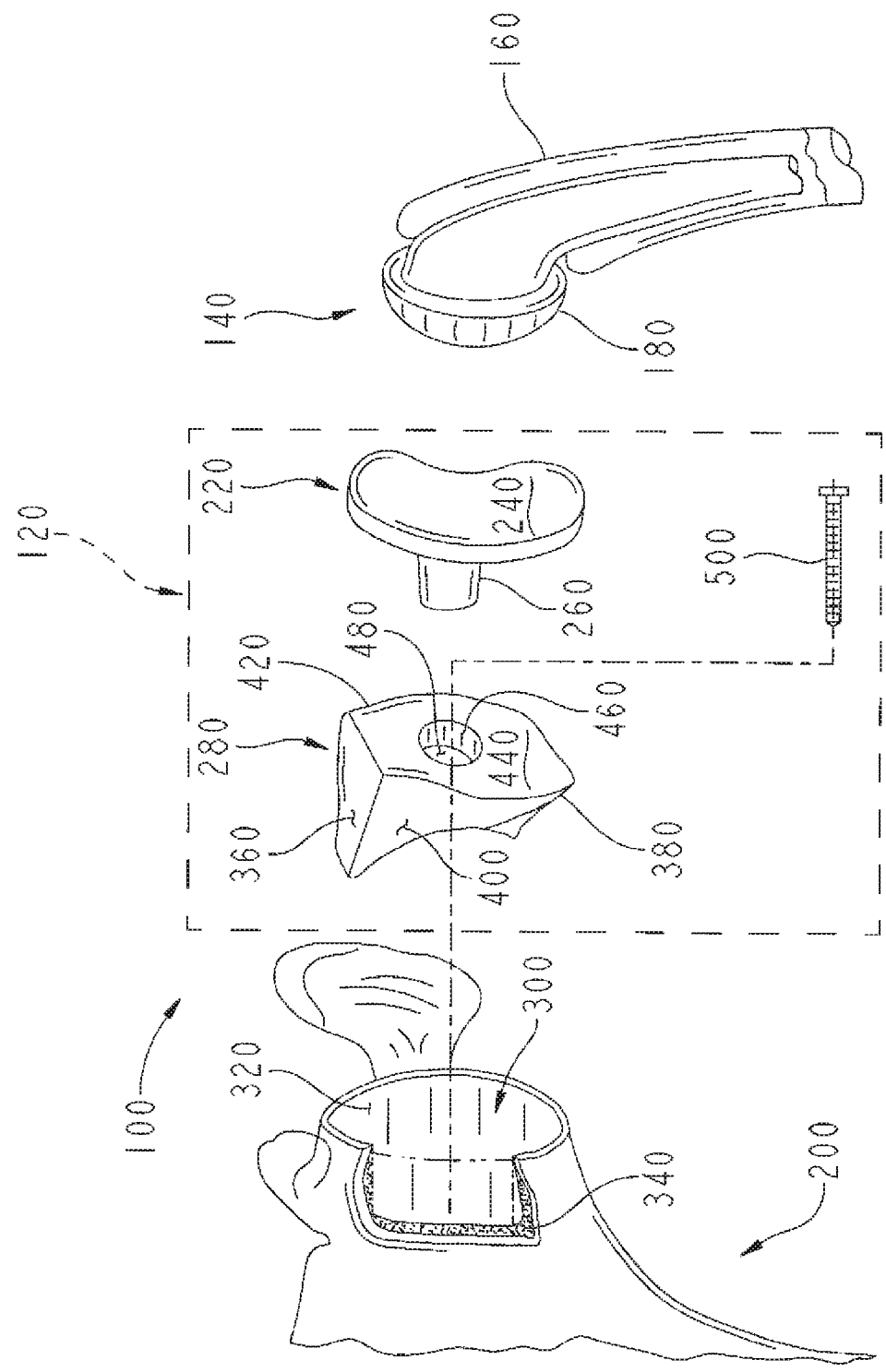
FIG. 1 shows an exploded perspective view of an exemplary shoulder prosthesis including an exemplary glenoid component according to the present invention.

Like reference numerals refer to like parts throughout the following description and the accompanying drawings.

FIG. 1 shows an exploded perspective view of an exemplary shoulder prosthesis 100 including an exemplary glenoid component 120 according to the present invention. Prosthesis 100 also includes an exemplary humeral component 140. Humeral component 140 is configured in a known manner for implantation in a humerus 160 and replacement of a natural humeral head (not shown) and, accordingly, includes a prosthetic humeral head 180.

Glenoid component 120 is configured for implantation in a scapula 200 and replacement of a natural glenoid fossa (not shown in FIG. 1). Glenoid component 120 includes a bearing 220. Bearing 220 is made from a durable biocompatible plastic or any other suitable durable biocompatible material. For example, bearing 220 may be made from a polyethylene. One particular polyethylene that is well suited for bearing 220 is a high molecular weight polyethylene, for example ultra-high molecular weight polyethylene ("UHMWPE"). One such UHMWPE is sold as by Johnson & Johnson of New Brunswick, N.J. as MARATHON™ UHMWPE and is more fully described in U.S. Pat. Nos. 6,228,900 and 6,281,264 to McKellop, which are incorporated herein by reference. Bearing 220 includes a generally concave surface 240 that is configured as known for bearing against prosthetic humeral head 180 or, in cases where the natural humeral head is spared, for bearing against the natural humeral head. Bearing 220 further includes a post 260, or some other feature or mechanism capable of mating the bearing to a stem element of the glenoid component, such as stem 280 discussed below.

Glenoid component 120 also includes a stem 280. As discussed further below, stem 280 is configured to model a normal or pathologic glenoid vault morphology such that stem 280 fits within a cavity 300 that may be defined, at least partially, by endosteal walls 320 of scapula 200. To this end, it is noted that the present invention may provide a series of rigidly scaled or sized versions of stem 280 for accommodating various glenoid vault sizes that may be presented among different patients. It should also be appreciated that the glenoid vault of scapula 200 may include some cancellous bone 340.

Stem 280 is made from a suitable biocompatible metal such as, for example, a cobalt chromium alloy, a stainless steel alloy, a titanium alloy, or any other suitable durable material. In alternative embodiments, stem 280 may include a porous coating to facilitate bone in-growth into glenoid component 120. The porous coating may be any suitable porous coating and may for example be POROCOAT®, a product of Johnson & Johnson of New Brunswick, N.J. and more fully described in U.S. Pat. No. 3,855,638 to Pilliar, which is incorporated herein by reference. Stem 280 can be solid or a thin shell of suitable durable material.

Stem 280 includes a generally superior surface 360, a generally inferior surface 380, a generally anterior-medial surface 400, a generally posterior-medial surface 420, and a generally lateral surface 440. Stem 280 defines a socket 460 that extends inwardly from surface 440. Socket 460 receives post 260 (of bearing 220). Stem 280 may also define a through-channel 480 that extends, coaxially with socket 460, through stem 280.

Glenoid component 120 further includes a fastener 500 in the form of, for example, a screw. The screw, or screws, may be any screw capable of additionally securing glenoid component 120 within scapula 200. For example, the screw may be a cortical screw such as DePuy Ace catalog number 8150-36-030 available from DePuy Orthopaedics, Inc. of Warsaw, Ind. The screw has a diameter sufficient to properly secure glenoid component 120 within scapula 200 and may, for example, have a diameter of about two to five millimeters. The screw may have any suitable length capable of properly securing glenoid component 120 within scapula 200. For example, the screw may have a length of from 10 to 60 millimeters. The screw may be secured to stem 280 in any suitable manner. In the exemplary embodiment, fastener 500 extends through through-channel 480 (of stem 280). However, it is noted that fastener 500 is not indispensable and may be omitted from alternative embodiments.

Bearing 220 is secured to stem 280 in any suitable manner. For example, bearing 220 may be bonded to stem 280, or bearing 220 could be made from polyethylene and compression molded to stem 280. Alternately, the bearing 220 may be glued to stem 280 by, for example, an adhesive. Alternatively, bearing 220 may be mechanically interlocked to stem 280 by taper locking or otherwise press-fitting post 260 in socket 460, or post 260 and socket 460 may include any other suitable interlocking features, for example, rib(s), lip(s), detent(s), and/or other protrusion(s) and mating groove(s), channel(s), or indent(s) (not shown). Additionally, it is noted that in alternative embodiments, bearing 220 and stem 280 may be integrated into a single part made from UHMWPE or any other suitable material—with or without an omission of fastener 500.

Figure 2A:
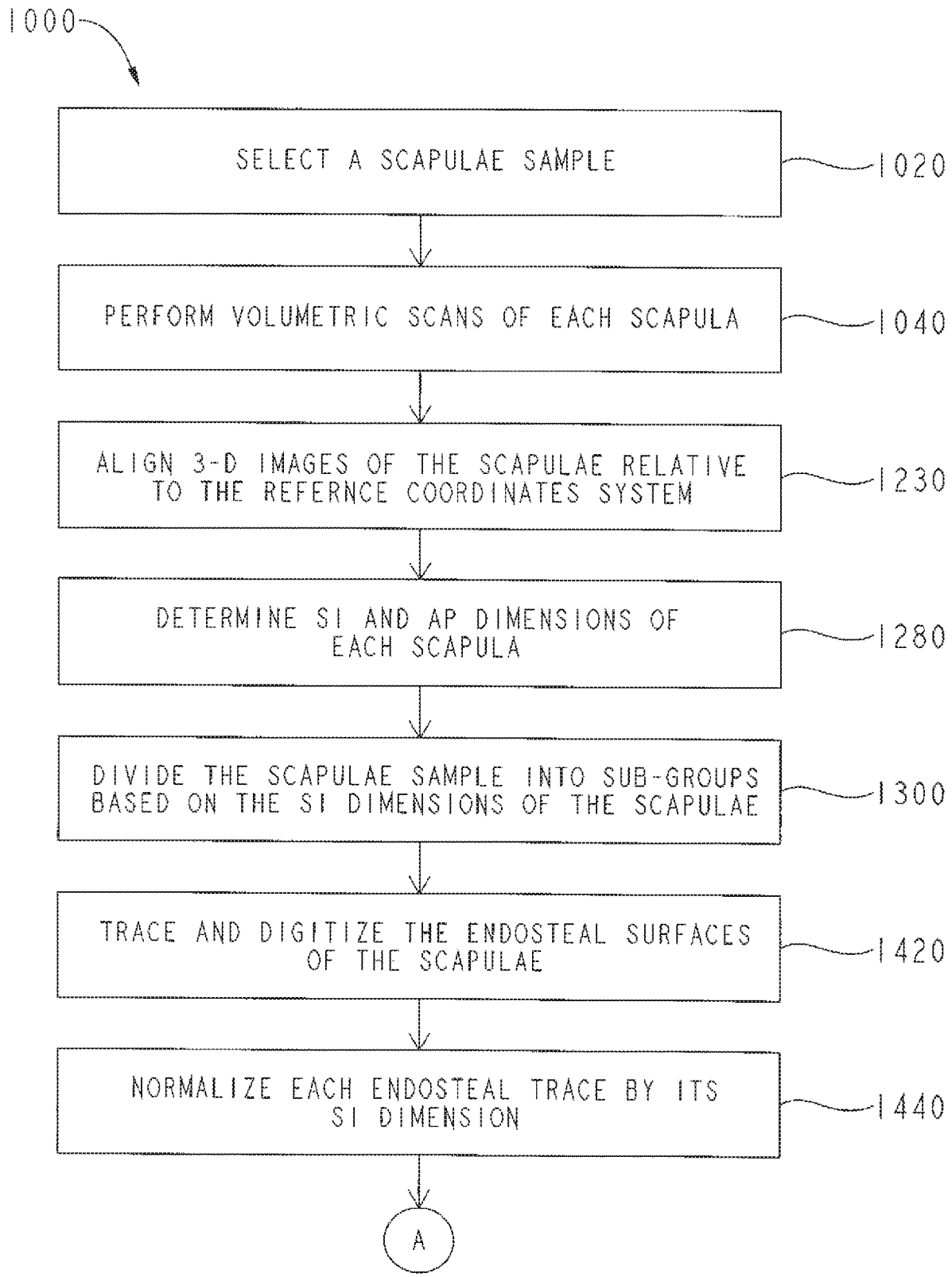
FIG. 2a, FIG. 2b, and FIG. 2c show a flow diagram of an exemplary method for configuring the stem of the prosthesis of FIG. 1 to model a normal or pathologic glenoid vault morphology.
Figure 2B:
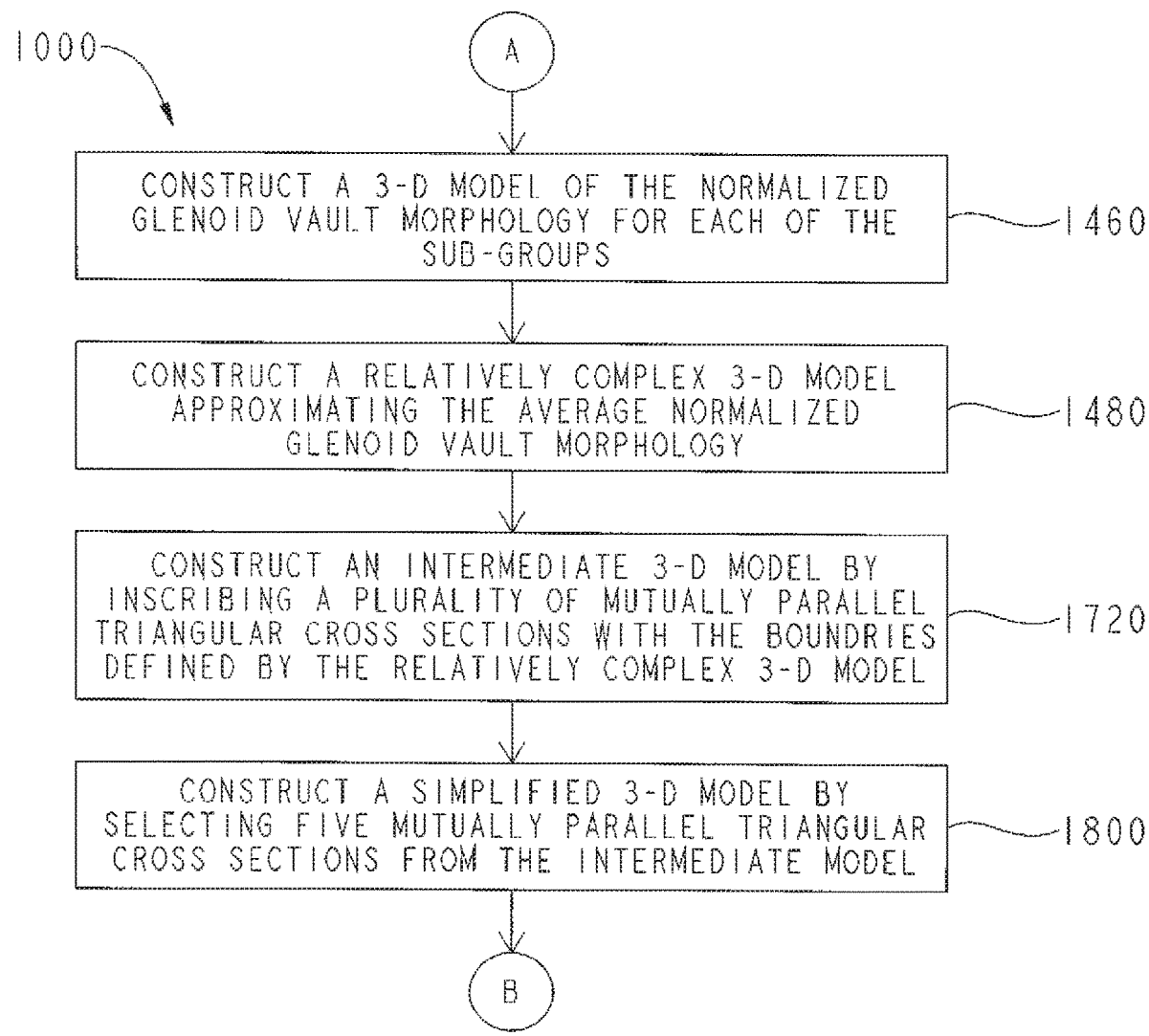
Figure 2C:
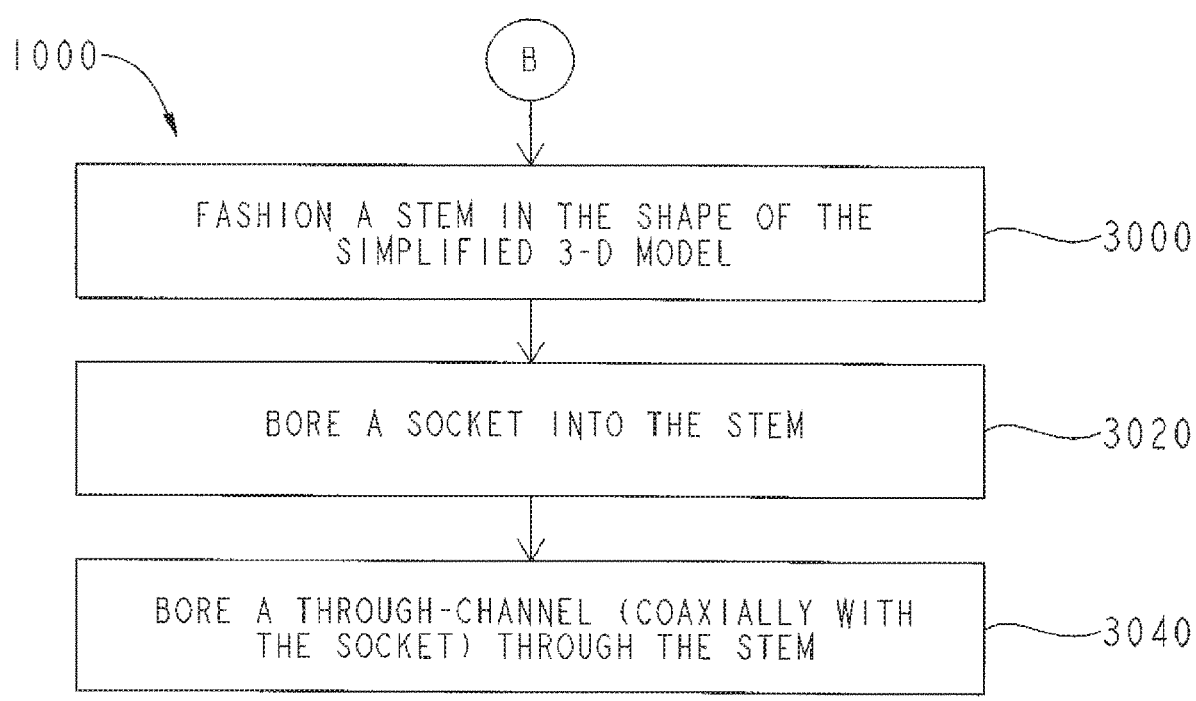

The present invention contemplates a method for preparing a glenoid component that will satisfy a majority of patient anatomies. Thus, in accordance with one method, the steps described in flow diagrams of FIGS. 2a-2c correspond to one exemplary method used to model the normal or pathologic glenoid vault morphology, and ultimately to prepare an optimally sized and configured implant.

In a first step 1020 (FIG. 2a), a suitable sample of human scapulae ("scapulae sample") is selected to represent a reasonable demographic cross section of an anticipated patient population. In the exemplary embodiment, the scapulae sample included sixty-one human scapulae selected from different sources, thirty-two left-sided and twenty-eight right-sided. Various criteria were applied to the selection process so that the sample was as representative of the patient population as possible, including height, sex, gender and ethnicity.

At step 1040 (FIG. 2a), volumetric scan of each scapula in the sample was performed using a Siemens Volume Zoom Scanner (a CT scanner available from Siemens Medical Systems of Malvern, Pa.). It is noted that the initial orientation of the scapulae in the CT images is dependent on the physical placement and orientation of the scapulae within the CT scanner, which is inherently difficult to reproduce. Nevertheless, the scapulae were placed in a supine anatomic position and axial images were obtained in one mm increments (with 0.27 to 0.35 mm in-plane resolution). The images were acquired at 120 kV, 100 mA, using a 180 mm field-of-view, large focal spot, and rotation speed of 0.5 sec/rev. A medium-smooth reconstruction algorithm was used for reconstruction of the images.

Figure 3:
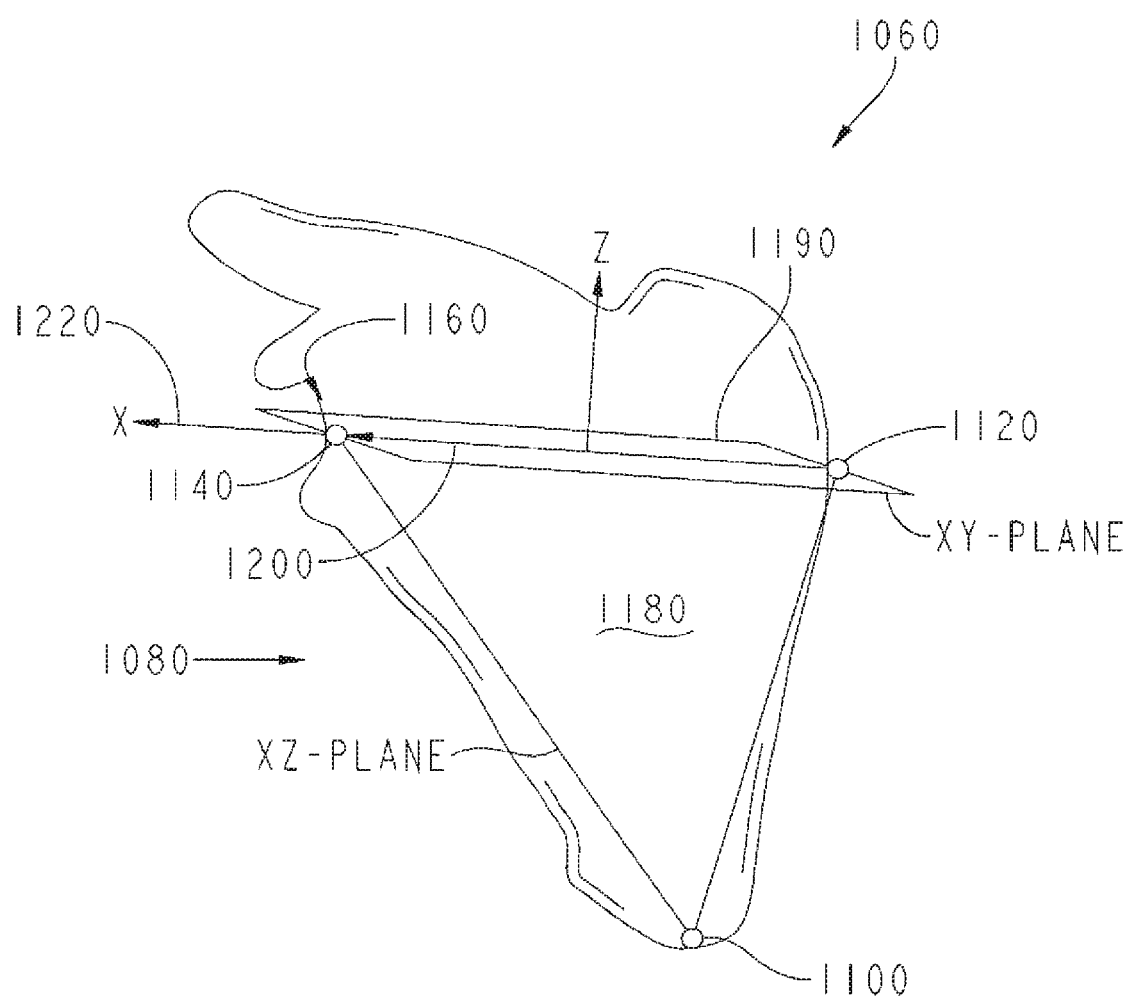
FIG. 3 shows a rectangular ("Cartesian") coordinates reference system relative to the plane body of a typical scapula as defined by three surface points of the scapula.

FIG. 3 shows a rectangular ("Cartesian") coordinates reference system 1060 relative to the plane body of a typical scapula 1080 as defined by three surface points 1100, 1120, and 1140 of the scapula 1080. As at least partially discernable from FIG. 3, point 1100 represents an inferior tip of the scapula 1080, point 1120 represents a medial pole of the scapula 1080 where the spine intersects the scapula 1080, and point 1140 represents the center of the typical glenoid fossa 1160. Further, it should be appreciated that coordinates reference system 1060 defines, among other things, an XZ-plane 1180, an XY-plane 1190, a vector 1200 extending from the medial pole of the scapula to the center of the glenoid fossa 1160, and an X-axis 1220.

At step 1230 (FIG. 2a), the three-dimensional ("3-D") images of the scapulae were re-sampled to align them on coordinates reference system 1060 (see FIG. 3) for subsequent analysis. In the exemplary embodiment, points 1100, 1120, and 1140 were interactively chosen on the 3-D image of each scapula and the scapulae were again re-sampled such that the plane of the body of each scapula was aligned parallel to the XZ-plane 1180 of the coordinates reference system 1060 (see FIG. 3), and such that the vector 1200 extending from the medial pole of the scapula to the center of the glenoid fossa 1160 was parallel to the X-axis 1220 (see FIG. 3).

Figure 4:
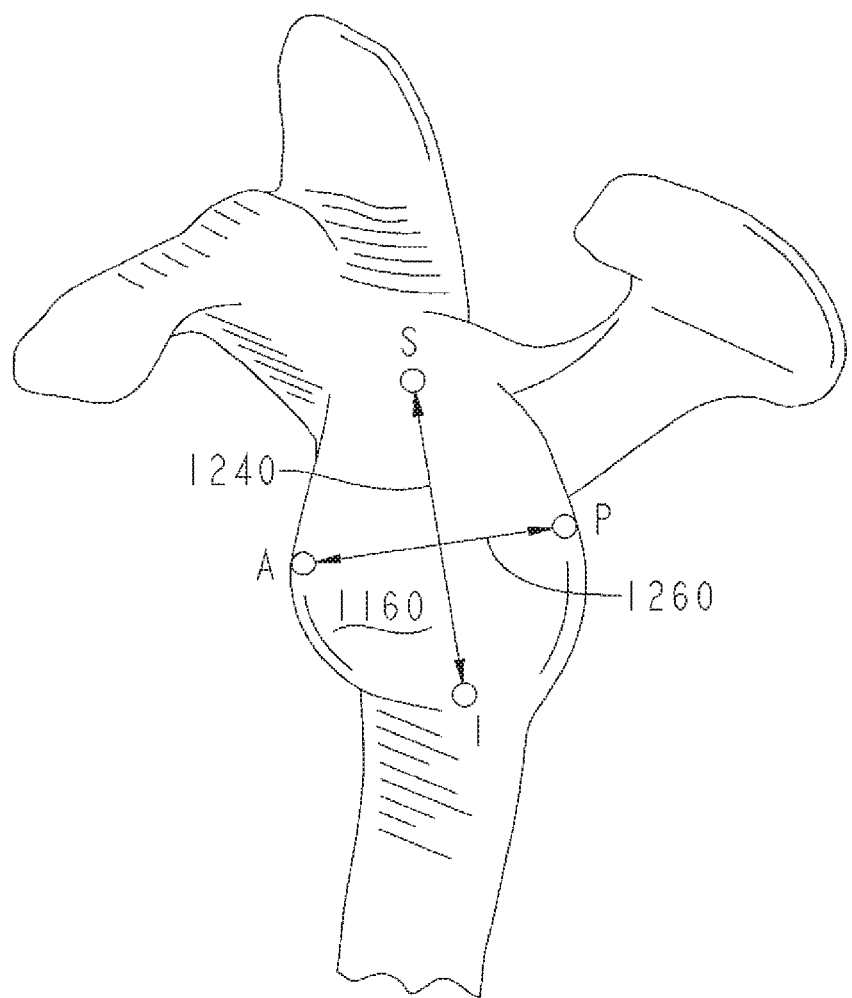
FIG. 4 shows the superior-inferior ("SI") dimension and the anterior-posterior ("AP") dimension of the typical glenoid fossa.

FIG. 4 shows the superior-inferior ("SI") dimension 1240 and the anterior-posterior ("AP") dimension 1260 of the glenoid fossa 1160. At step 1280 (FIG. 2a), the SI dimension 1240 and the AP dimension 1260 (see FIG. 4) of each scapula was determined by interactively placing points on the 3-D images using a suitable software program.

At step 1300 (FIG. 2a), the scapulae sample were arbitrarily divided into six sub-groups based on their SI dimensions 1240 (see FIG. 4) to reduce the initial number of morphological comparisons and to facilitate determination of the relationship between the global or overall typical glenoid vault size and the typical glenoid vault morphology. FIG. 5 shows a table listing exemplary range and exemplary average SI dimension for the six sub-groups of scapulae based on their SI dimensions.

Figure 6:
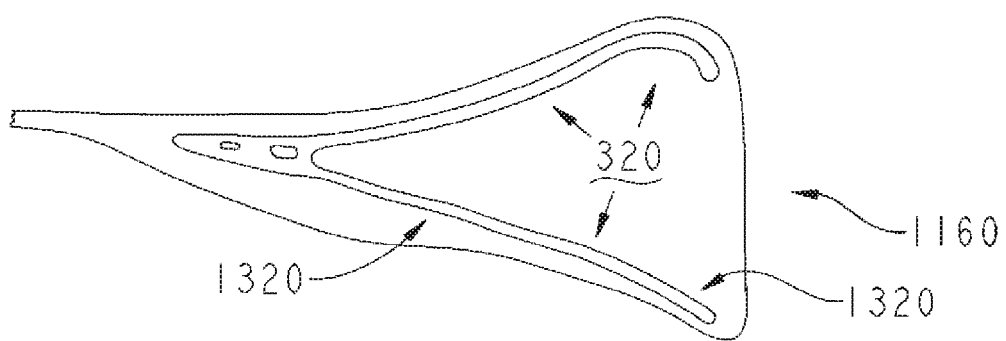
FIG. 6 shows an exemplary substantially complete tracing (toward the inferior end of the typical glenoid fossa) of the endosteal walls of the typical glenoid fossa.
Figure 7:
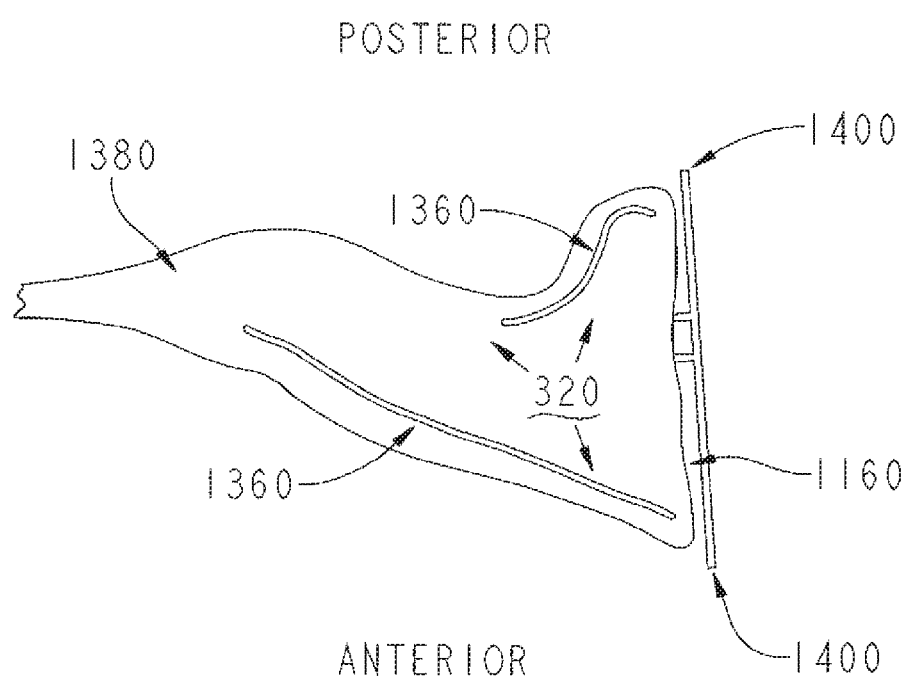
FIG. 7 shows an exemplary partial tracing (toward the inferior end of the typical glenoid fossa) of the endosteal walls of the typical glenoid fossa as a result of fossa occlusion in the region of the typical scapular spine.

At step 1420 (FIG. 2a), the endosteal walls 320 of the glenoid vaults of the scapulae were manually traced and digitized. FIG. 6 shows a substantially complete tracing 1320 (toward the inferior end of the typical glenoid fossa 1160) of the endosteal walls 320 of the typical glenoid fossa 1160. FIG. 7 shows a partial tracing 1360 (toward the inferior end of the typical glenoid fossa 1160) of the endosteal walls 320 of the typical glenoid fossa 1160 as a result of fossa occlusion in the region of the typical scapular spine 1380. Reference line 1400 (FIG. 7) is discussed further below. Each endosteal boundary was traced on each of the two-dimensional ("2-D") XY-slices of the respective re-sampled image (see FIG. 6), starting at the respective glenoid fossa and extending medially to the scapular spine 1380 (see FIG. 7), but not into the interior of the spine. Both the anterior and posterior wall tracings in the region of the spine are terminated at reference line 1400 (see FIG. 7), which was defined to be simultaneously perpendicular to the plane of the respective glenoid fossa and tangential to the surface of the respective endosteal notch.

At step 1440 (FIG. 2a), each endosteal tracing defining the respective glenoid vault was normalized by its extent in the SI dimension. This measurement was made from the inferior limit of the endosteal walls of the glenoid fossa to the superior limit in the Z-dimension (see FIG. 3) of the image. The vaults were rigidly scaled in all three dimensions (i.e., X, Y, and Z) to normalize the SI dimension of the vault tracing to the average within its corresponding sub-grouping. This approach substantially eliminated size differences between the different vaults, facilitating an appropriate shape determination. An assumption was made that right-sided and left-sided scapulae are approximately anatomically symmetrical. Under this assumption, right-sided vaults were mirrored about the XZ-plane (see FIG. 3) to allow morphological determinations to be made within the entire sample. In the exemplary embodiment, the normalized vaults within each of the six scapular sub-groupings were spatially aligned (i.e., "registered") using an iterative closet point ("ICP") algorithm such as discussed in Besl P. J. and McKay N. D., "A method for registration of 3-D shapes," IEEE Trans. Pattern Analysis and Machine Intelligence 1992, volume 14, pages 239-256, which is incorporated herein by reference.

At step 1460 (FIG. 2b), a 3-D model of the normalized glenoid vault morphology was then constructed for each sub-group of the scapulae of the scapulae sample based on the morphological constraints imposed by each of the vaults in the sub-group. For each sub-group, the set of registered glenoid vaults were overlaid and the approximate average endosteal walls 320 (see FIG. 6 and FIG. 7) of the sub-group were manually digitized. Each endosteal boundary was traced on each of the two-dimensional ("2-D") XY-slices of the respective re-sampled image (see FIG. 6), starting at the respective glenoid fossa and extending medially to the scapular spine 1380 (see FIG. 7), but not into the interior of the spine. Both the anterior and posterior wall tracings in the region of the spine were terminated at reference line 1400 (see FIG. 7), which was defined to be simultaneously perpendicular to the plane of the respective glenoid fossa and tangential to the surface of the respective endosteal notch. The resulting 3-D model satisfied the endosteal wall boundaries for each vault within the group.

At step 1480 (FIG. 2b), a relatively complex 3-D model 1500 (see FIG. 8) approximating the average normalized glenoid vault morphology of the entire scapulae sample was constructed based on the morphological constraints imposed by the models for each sub-group. The registered glenoid vaults for the sub-groups were overlaid and the approximate average endosteal walls 320 (see FIG. 6 and FIG. 7) of the sub-group models were manually digitized. Each endosteal boundary was again traced on each of the two-dimensional ("2-D") XY-slices of the respective re-sampled image (see FIG. 6), starting at the respective glenoid fossa and extending medially to the scapular spine 1380 (see FIG. 7), but not into the interior of the spine. Both the anterior and posterior wall tracings in the region of the spine were terminated at reference line 1400 (see FIG. 7), which was defined to be simultaneously perpendicular to the plane of the respective glenoid fossa and tangential to the surface of the respective endosteal notch. The resulting 3-D model 1500 satisfies the endosteal wall boundaries for each vault within the scapulae sample.

Figure 8:
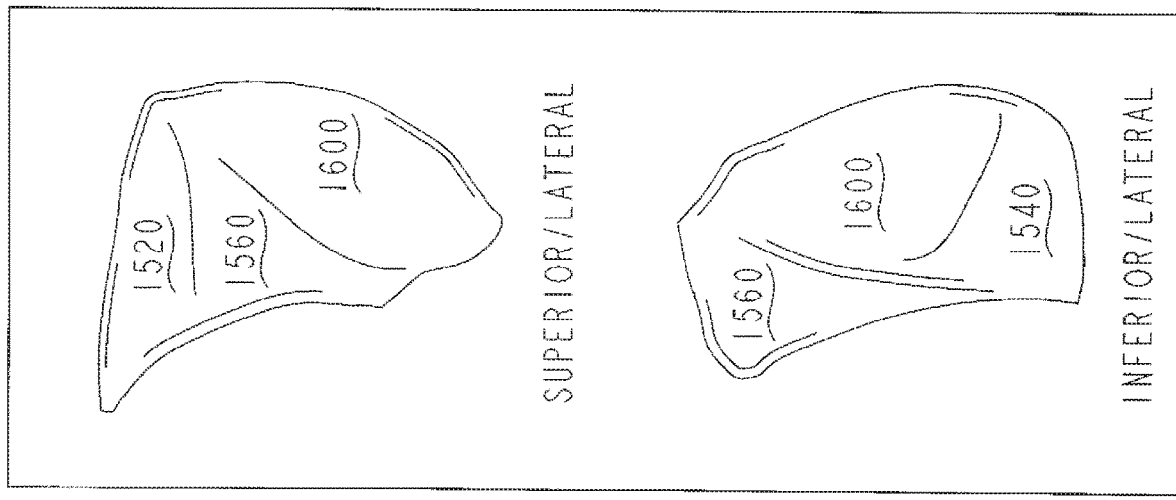
FIG. 8 shows views of a volumetric rendering of a relatively complex model of the normal glenoid vault morphology of the scapulae sample.
Figure 8:
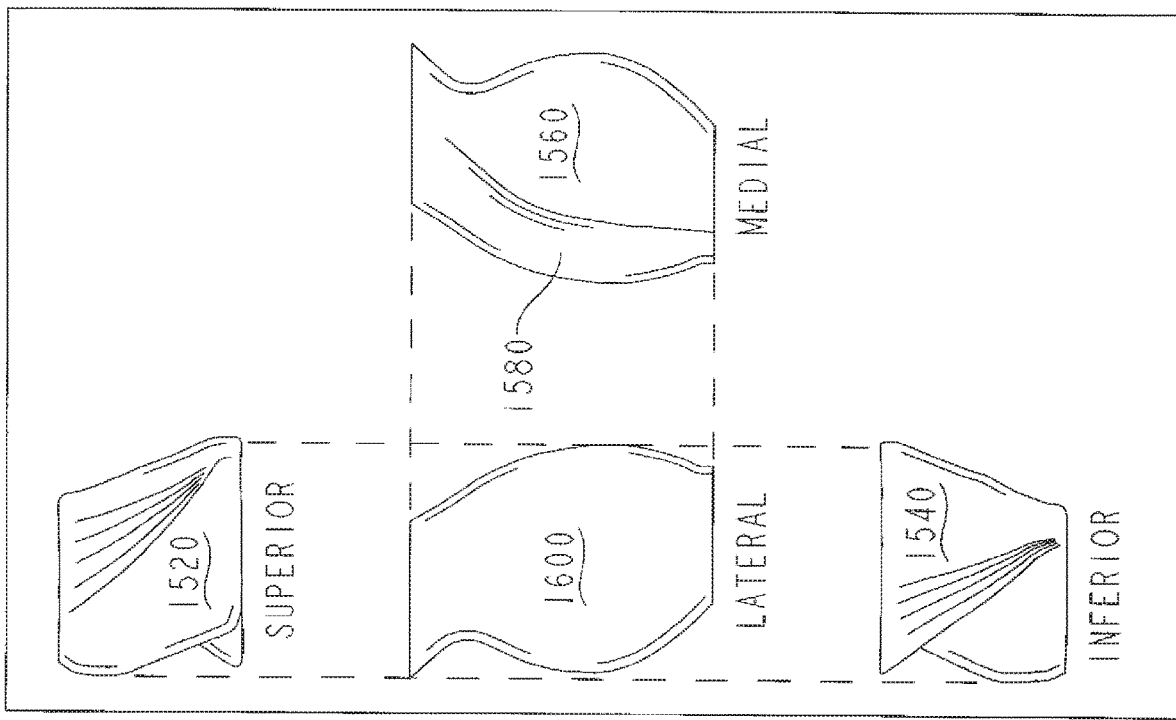

FIG. 8 shows views of a volumetric rendering of the relatively complex 3-D model 1500 generated in the previous steps. As at least partially discernable in FIG. 8, model 1500 includes a generally superior surface 1520, a generally inferior surface 1540, a generally anterior-medial surface 1560, a generally posterior-medial surface 1580, and a generally lateral surface 1600. It should be appreciated that generally superior surface 360 (of stem 280) corresponds roughly to generally superior surface 1520, generally inferior surface 380 (of stem 280) corresponds roughly to generally inferior surface 1540, generally anterior-medial surface 400 (of stem 280) corresponds roughly to generally anterior-medial surface 1560, generally posterior-medial surface 420 (of stem 280) corresponds roughly to generally posterior-medial surface 1580, and generally lateral surface 440 (of stem 280) corresponds roughly to generally lateral surface 1600.

Figure 9:
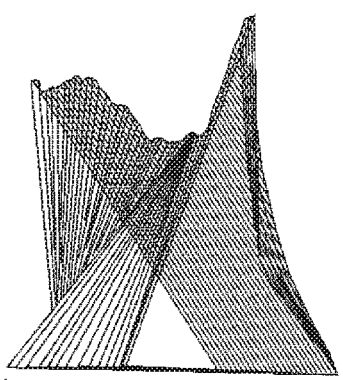
FIG. 9 shows views of a volumetric rendering of an intermediate 3-D model of the normal glenoid vault morphology of the scapulae sample based on the relatively complex 3-D model of FIG. 8.
Figure 9:
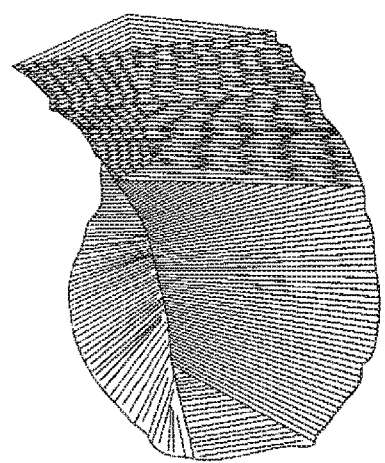
Figure 9:
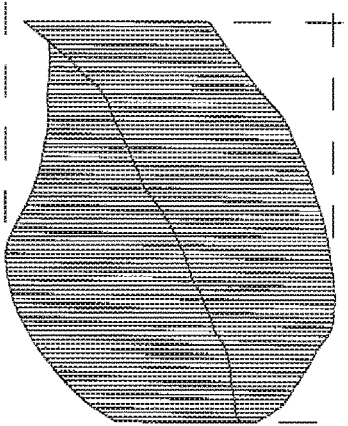
Figure 9:
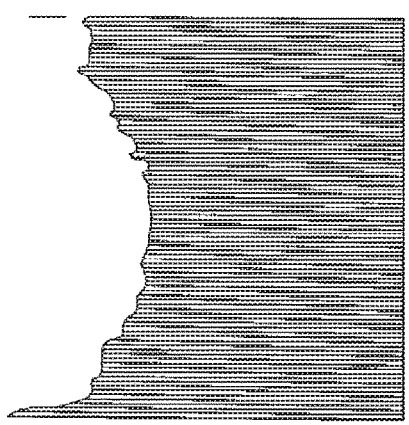

At step 1720 (FIG. 2b), intermediate 3-D model 1700 was constructed by inscribing a plurality of mutually parallel triangular cross sections within the boundaries defined by the model walls on a plurality of XY-plane (see FIG. 3) cross-sections of relatively complex 3-D model 1500 (see FIG. 8). FIG. 9 shows views of a volumetric rendering of this intermediate 3-D model 1700 of the normalized glenoid vault morphology of the scapulae sample based on relatively complex 3-D model 1500 (see FIG. 8).

At step 1800 (FIG. 2b), a simplified 3-D model 1820 (see FIG. 10) of the average normalized glenoid vault morphology of the scapulae sample was constructed by selecting five equidistantly inferior-superior spaced-apart mutually parallel triangular cross sections (1840, 1860, 1880, 1900, 1920) (see FIGS. 10 and 11) from intermediate 3-D model 1700 (see FIG. 9). These triangular cross-sections were selected to account for more than 90% of the volume of intermediate 3-D model 1700 with almost negligible spatial deviation of the anterior and posterior walls. It should be appreciated that simplified 3-D model 1820 thus provides a concise geometrical model of the normalized glenoid vault morphology while substantially preserving the morphological nuances inherent to the endosteal walls 320 (see FIG. 1).

Figure 10:
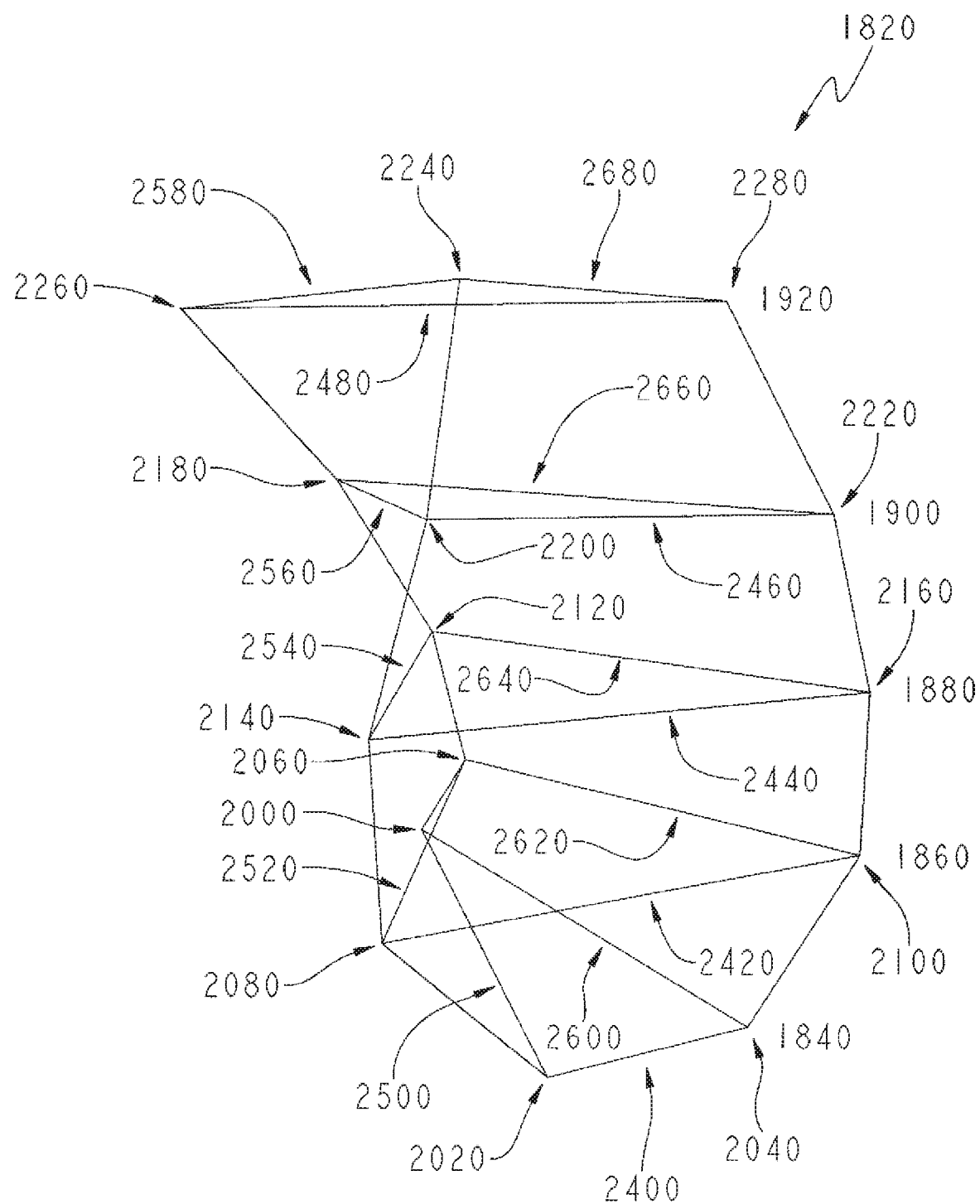
FIG. 10 shows a perspective view of a simplified 3-D model of the average normal glenoid vault morphology of the scapulae sample based on the intermediate 3-D model of FIG. 9.
Figure 11:
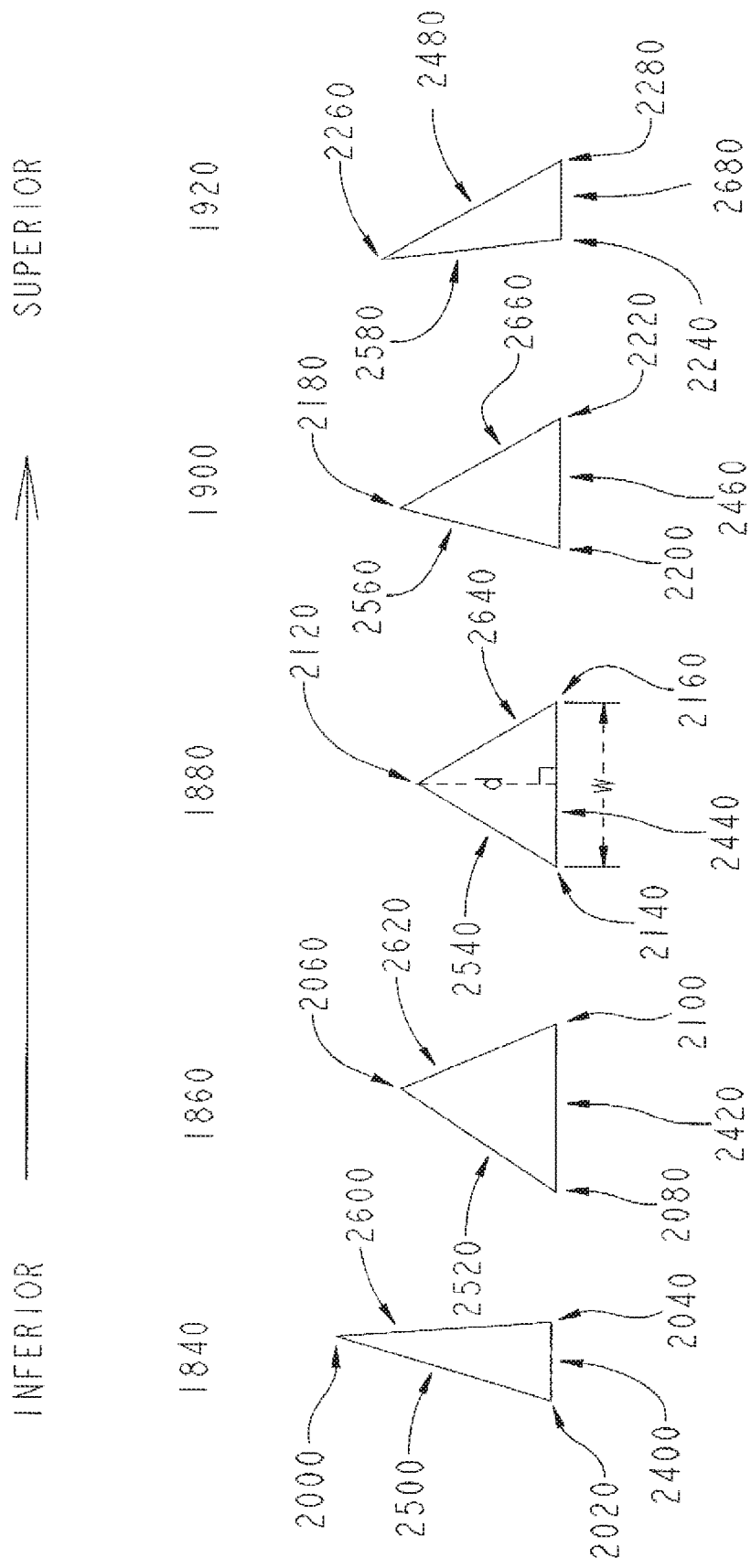
FIG. 11 shows a superior view of each of the triangular cross sections of the simplified 3-D model of FIG. 10.

A perspective view of this simplified 3-D model 1820 of the average normalized glenoid vault morphology of the scapulae sample is shown in FIG. 10. FIG. 11 shows a superior view of each of the triangular cross sections (1840, 1860, 1880, 1900, 1920) obtained from the simplified 3-D model 1820. As at least partially discernable from FIGS. 10 and 11, cross section 1840 includes a generally medially positioned vertex 2000, a generally anteriorly and generally laterally positioned vertex 2020, and a generally posteriorly and generally laterally positioned vertex 2040. Similarly, cross section 1860 includes a generally medially positioned vertex 2060, a generally anteriorly and generally laterally positioned vertex 2080, and a generally posteriorly and generally laterally positioned vertex 2100. Cross section 1880 includes a generally medially positioned vertex 2120, a generally anteriorly and generally laterally positioned vertex 2140, and a generally posteriorly and generally laterally positioned vertex 2160. The next cross section 1900 includes a generally medially positioned vertex 2180, a generally anteriorly and generally laterally positioned vertex 2200, and a generally posteriorly and generally laterally positioned vertex 2220. Finally, cross section 1920 includes a generally medially positioned vertex 2240, a generally anteriorly and generally laterally positioned vertex 2260, and a generally posteriorly and generally laterally positioned vertex 2280.

Further, cross section 1840 includes a "base" edge 2400 extending between vertex 2020 and vertex 2040, cross section 1860 includes a "base" edge 2420 extending between vertex 2080 and vertex 2100, cross section 1880 includes a "base" edge 2440 extending between vertex 2140 and vertex 2160, cross section 1900 includes a "base" edge 2460 extending between vertex 2200 and vertex 2220, and cross section 1920 includes a "base" edge 2680 extending between vertex 2240 and vertex 2280.

In addition, cross section 1840 includes a "left" edge 2500 extending between vertex 2000 and vertex 2020, cross section 1860 includes a "left" edge 2520 extending between vertex 2060 and vertex 2080, cross section 1880 includes a "left" edge 2540 extending between vertex 2120 and vertex 2140, cross section 1900 includes a "left" edge 2560 extending between vertex 2180 and vertex 2200, and cross section 1920 includes a "left" edge 2580 extending between vertex 2240 and vertex 2260.

Finally, cross section 1840 includes a "right" edge 2600 extending between vertex 2000 and vertex 2040, cross section 1860 includes a "right" edge 2620 extending between vertex 2060 and vertex 2100, cross section 1880 includes a "right" edge 2640 extending between vertex 2120 and vertex 2160, cross section 1900 includes a "right" edge 2660 extending between vertex 2180 and vertex 2220, and cross section 1920 includes a "right" edge 2480 extending between vertex 2260 and vertex 2280.

The respective base edges (2400, 2420, 2440, 2460, 2680) of the triangular cross sections (1840, 1860, 1880, 1900, 1920) define lateral boundaries of simplified 3-D model 1820, corresponding to the region of the typical glenoid fossa 1160 (see FIG. 3). Further, the respective left edges (2500, 2520, 2540, 2560, 2580) of triangular cross sections (1840, 1860, 1880, 1900, 1920) define anterior boundaries of simplified 3-D model 1820, while the respective "right" edges (2600, 2620, 2640, 2660, 2480) of triangular cross sections (1840, 1860, 1880, 1900, 1920) define posterior boundaries of simplified 3-D model 1820. The respective generally medially positioned vertexes (2000, 2060, 2120, 2180, 2260) of triangular cross sections (1840, 1860, 1880, 1900, 1920) sweep from a more posterior orientation at the inferior end of simplified 3-D model 1820 to a more anterior orientation at the superior end of simplified 3-D model 1820.

Each of the triangular cross sections (1840, 1860, 1880, 1900, 1920) has a respective width dimension ("w") and a depth dimension ("d"). The table in FIG. 12 summarizes the respective width dimension ("w") (see FIG. 11), depth dimension ("d") (see FIG. 11), and resulting area of triangular cross sections (1840, 1860, 1880, 1900, 1920). The table in FIG. 13 lists the coordinates for the respective vertexes of triangular cross sections (1840, 1860, 1880, 1900, 1920) relative to rectangular ("Cartesian") coordinates reference system 1060 (see FIG. 3).

It is contemplated that simplified 3-D model 1820 may be rigidly scaled according to SI size (see FIG. 4) to accommodate larger or smaller glenoid vaults while maintaining the integrity of the basic morphological model.

At step 3000 (FIG. 2c), stem 280 is initially fashioned in the shape of the simplified 3-D model 1820. In one embodiment, this step 3000 contemplates loading the coordinates of each of the vertexes defining the simplified 3-D geometrical model 1820 into a suitable stereo lithography system. The stereo lithography system may be operated to produce a corresponding 3-D form made of a plastic, wax, or any other suitable material as is known in the art. A mold is then prepared from the 3-D form and a stem 280 is fashioned, such as by injection molding using this mold. In alternative embodiments stem 280 may be otherwise suitably produced in accordance with simplified 3-D model 1820 via stereo lithography, by hand, or by any other suitable method (with or without an intervening form or mold) as known.

In subsequent steps, the stem 280 is machined to provide the features necessary to prepare the stem for implantation.

Thus, at step 3020 (FIG. 2c), socket 460 is bored into stem 280. At step 3040 (FIG. 2c), through-channel 480 is bored (coaxially with socket 460) through stem 280. It should be understood that the rough stem produced from the 3-D model may be machined according to other protocols depending upon the interface between the stem 280 and the bearing 220. It is further contemplated that the stem 280 may be formed as a solid or a hollow body and may further be provided with certain surface features to facilitate fixation of the stem within the glenoid vault.

The improved stem may then be implanted in accordance with known surgical procedures. For instance, cancellous bone 340 may first be removed from the glenoid vault of scapula 200 to construct cavity 300, which extends to endosteal walls 320 (see FIG. 1). Stem 280 is then inserted into cavity 300 into intimate contact with endosteal walls 320 to facilitate alignment and reliable fixation of glenoid component 120 within scapula 200. Bone cement may be used to enhance fixation of the stem within the bone. Fastener 480 is inserted through through-channel 480 into engagement with scapula 200. After fastener 480 is fully inserted into scapula 200, post 260 is inserted into socket 460 and bearing 220 is secured to stem 280.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

For example, the glenoid components may be solid or hollow bodies. In particular, the stem 280 may be formed as a solid implant, but may be preferably at least partially hollow to reduce the weight and material requirements for the component. If the implant component is hollow, it must have sufficient wall thickness to maintain its strength and integrity under maximum expected physiological loads.

The present invention contemplates a glenoid stem component that is formed to closely approximate a normalized glenoid vault morphology. In the embodiments discussed above, this normalized morphology is generated from a relatively large sample size of human scapulae from which relevant measurements were obtained. It was found that the normalized component dimensions obtained in accordance with the invention well approximated the actual dimensions of the sample population. In particular, it was found that at least 85% of the surface points of the sampled glenoid vaults varied by less than 2.0 mm, which represents a minimal variation given the overall dimensions of the endosteal walls of the vault.

In generating the vault models for the different groups noted above, it was discovered that for the entire set of vault geometries, 98.5% of the surface points comprising the interior surface models varied by less than 2.0 mm. This finding refuted a prior assumption that vault morphology was dependent upon the global vault size. As a result, a single vault model was derived from the group models using the same steps described above. This final model is depicted in FIG. 9. From that model of the actual glenoid vault morphology for the entire sample population, the simplified geometric model was developed as described above. This simplified model was found to account for over 80% of the volume of the model of the actual sample population, while also preserving the morphological nuances inherent to the endosteal surfaces of the glenoid vault.

In one aspect of the invention, a morphological model is developed for several discrete groups of glenoid sizes. The groups may be preferably grouped by SI (superior-inferior) dimension, as summarized in the table of FIG. 5. The simplified model used to create the component mold in the illustrated embodiment corresponded to Group 4, but it is understood that the simplified model for the other groups may be obtained by directly scaling the dimensions as a function of the ratio of SI values.

What is claimed is:

1. A glenoid component, comprising:
    a laterally facing bearing surface configured to engage a bearing surface of an element associated with a humerus; and
    a stem portion extending medially away from the bearing surface, wherein the stem portion is configured such that when implanted in a scapula the stem portion includes
        a first cross-section in an XY-plane perpendicular to an XZ-plane, wherein the XZ-plane is defined by an inferior tip of the scapula, a medial pole of the scapula where a spine intersects the scapula, and the center of the glenoid fossa,
        a second cross-section parallel to the first cross-section and inferior to the first cross-section, and
        a third cross-section parallel to the first cross-section and superior to the first cross-section, wherein
    the first cross-section is shaped based upon a first triangle having a first length in the XY-plane along an X-axis defined by the medial pole of the scapula and the center of the glenoid fossa of the scapula,
    the second cross-section is shaped based upon a second triangle having a second length along the X-axis,
    the third cross-section is shaped based upon a third triangle having a third length along the X-axis, and
    the first length is shorter than the second length and shorter than the third length.

2. The glenoid component of claim 1, wherein the stem portion further comprises:
    a fourth cross-section parallel to the first cross-section, inferior to the first cross-section, and superior to the second cross-section, and
    a fifth cross-section parallel to the first cross-section, superior to the first cross-section, and inferior to the third cross-section, wherein
    the fourth cross-section is shaped based upon a fourth triangle having a fourth length along the X-axis,
    the fifth cross-section is shaped based upon a fifth triangle having a fifth length along the X-axis, and
    the first length is shorter than the fourth length and shorter than the fifth length.

3. The glenoid component of claim 2, wherein the third length is longer than the second length, the fourth length, and the fifth length.

4. The glenoid component of claim 3, wherein the second length is longer than the fourth length, and the fifth length.

5. The glenoid component of claim 3, wherein:
    the first triangle defines a first area;
    the second triangle defines a second area;
    the third triangle defines a third area;
    the fourth triangle defines a fourth area;
    the fifth triangle defines a fifth area; and
    the fifth area is larger than the first area, the second area, the third area, and the fourth area.

6. The glenoid component of claim 5, wherein the second area is smaller than the first area, the third area, and the fourth area.

7. The glenoid component of claim 6, wherein the fourth area is larger than the first area, and the third area.

8. A glenoid component, comprising:

a laterally facing bearing surface configured to engage a bearing surface of an element associated with a humerus; and a stem portion extending medially away from the bearing surface, wherein the stem portion is configured such that when implanted in a scapula the stem portion includes a first cross-section parallel to an XY-plane including an X-axis defined by a medial pole of the scapula and the center of a glenoid fossa of the scapula, the XY-plane perpendicular to an XZ-plane defined by an inferior tip of the scapula, the medial pole of the scapula where a spine intersects the scapula, and the center of the U glenoid fossa, a second cross-section parallel to the first cross-section and inferior to the first cross-section, and a third cross-section parallel to the first cross-section and superior to the first cross-section, wherein the first cross-section is shaped based upon a first triangle having a first area, the second cross-section is shaped based upon a second triangle having a second area, the third cross-section is shaped based upon a third triangle having a third area, and the first area is smaller than the second area and smaller than the third area.

9. The glenoid component of claim 8, wherein the stem portion further comprises:

a fourth cross-section parallel to the first cross-section, inferior to the first cross-section, and inferior to the second cross-section, and a fifth cross-section parallel to the first cross-section, superior to the first cross-section, and superior to the third cross-section, wherein the fourth cross-section is shaped based upon a fourth triangle having a fourth area, the fifth cross-section is shaped based upon a fifth triangle having a fifth area, and the fifth area is larger than the fourth area and smaller than the first area.

10. The glenoid component of claim 9, wherein:

the first triangle defines a first length along the X-axis;

the second triangle defines a second length along the X-axis;

the third triangle defines a third length along the X-axis;

the fourth triangle defines a fourth length along the X-axis;

the fifth triangle defines a fifth length along the X-axis; and the first length is shorter than the second length, the third length, the fourth length, and the fifth length.

11. The glenoid component of claim 10, wherein:

the fifth length is larger than the second length, and the third length; and the fifth area is smaller than the first area, the second area, and the third area.

12. The glenoid component of claim 8, wherein:

the first triangle defines a first length along the X-axis;

the second triangle defines a second length along the X-axis;

the third triangle defines a third length along the X-axis;

the third area is larger than the second area; and the second length is longer than the third length.

* * * * *